(12) United States Patent
Nie et al.

(10) Patent No.: US 12,281,066 B1
(45) Date of Patent: Apr. 22, 2025

(54) DEVICE AND PROCESS FOR PREPARING SEBACIC ACID THROUGH ELECTROMAGNETIC INDUCTION HEATING COUPLED WITH DRY CONSTANT-TEMPERATURE ALKALINE HYDROLYSIS

(71) Applicant: ZHEJIANG UNIVERSITY OF TECHNOLOGY, Zhejiang (CN)

(72) Inventors: Yong Nie, Zhejiang (CN); Shangzhi Yu, Zhejiang (CN); Qianhui Weng, Zhejiang (CN); Hua Zhang, Zhejiang (CN); Zhendong Liu, Zhejiang (CN)

(73) Assignee: ZHEJIANG UNIVERSITY OF TECHNOLOGY, Zhejiang (CN)

( * ) Notice: Subject to any disclaimer, the term of this patent is extended or adjusted under 35 U.S.C. 154(b) by 0 days.

(21) Appl. No.: 18/896,739

(22) Filed: Sep. 25, 2024

(30) Foreign Application Priority Data

Jun. 3, 2024 (CN) .......................... 202410705381.7

(51) Int. Cl.
 *C07C 51/09* (2006.01)
 *B01J 8/08* (2006.01)
 *B01J 8/10* (2006.01)

(52) U.S. Cl.
 CPC ............... *C07C 51/09* (2013.01); *B01J 8/082* (2013.01); *B01J 8/085* (2013.01); *B01J 8/087* (2013.01); *B01J 8/10* (2013.01); *B01J 2208/00061* (2013.01); *B01J 2208/00433* (2013.01)

(58) Field of Classification Search
 None
 See application file for complete search history.

(56) References Cited

U.S. PATENT DOCUMENTS

2021/0115339 A1*  4/2021  Nie .......................... B01J 6/008

FOREIGN PATENT DOCUMENTS

| CN | 110963909 | 4/2020 |
|----|-----------|--------|
| CN | 212894515 | 4/2021 |

OTHER PUBLICATIONS

Machine generated English language translation of CN 110963909 ( published on Apr. 7, 2020) (Year: 2020).*

(Continued)

*Primary Examiner* — Amy C Bonaparte
(74) *Attorney, Agent, or Firm* — JCIPRNET

(57) ABSTRACT

The present disclosure relates to a device and process for preparing sebacic acid through electromagnetic induction heating coupled with dry constant-temperature alkaline hydrolysis. The device includes an electromagnetic heating cylinder and a reaction kettle arranged in the electromagnetic heating cylinder, heat storage pellets fill space between the reaction kettle and the electromagnetic heating cylinder, and the heat storage pellets adhere to an inner wall of the electromagnetic heating cylinder and an outer wall of the reaction kettle. The upper end of the reaction kettle is provided with a feeding port, a gas outlet and a temperature measuring port, the reaction kettle is also provided with a stirring device, a lower portion of the reaction kettle is provided with a discharging port, and the feeding port, the gas outlet, the temperature measuring port and the discharging port all extend out of the thermal insulation cotton.

7 Claims, 3 Drawing Sheets

(56) References Cited

OTHER PUBLICATIONS

Machine generated English language translation of CN 212894515 ( published on Apr. 6, 2021) (Year: 2021).*
Cornils ("Dicarboxylic Acids, Aliphatic" Ullmann's Encyclopedia of Industrial Chemistry, 2014, p. 1-18) (Year: 2014).*
Cotton (Merriam Webster, downloaded from https://www.merriam-webster.com/dictionary/cotton on Nov. 15, 2024) (Year: 2024).*
CF2517 Aluminum Silicate Sprayed Fiber Cotton (Standford Advanced Materials, downloaded from https://www.samaterials.com/ceramic-material/2517-aluminum-silicate-sprayed-fiber-cotton.html on Nov. 14, 2024) (Year: 2024).*

* cited by examiner

DEVICE AND PROCESS FOR PREPARING SEBACIC ACID THROUGH ELECTROMAGNETIC INDUCTION HEATING COUPLED WITH DRY CONSTANT-TEMPERATURE ALKALINE HYDROLYSIS

CROSS-REFERENCE TO RELATED APPLICATION

This application claims the priority benefit of China application serial no. 202410705381.7, filed on Jun. 3, 2024. The entirety of the above-mentioned patent application is hereby incorporated by reference herein and made a part of this specification.

TECHNICAL FIELD

The present disclosure relates to a device and process for preparing sebacic acid through electromagnetic induction heating coupled with dry constant-temperature alkaline hydrolysis.

BACKGROUND

Sebacic acid can be used for preparing high value-added fine chemical products such as bio-based engineering plastics, high-temperature-resistant lubricating oil, cosmetics and spices. At present, industrial production of the sebacic acid is mainly performed by an alkali fusion cracking method and a microbial fermentation method, and the microbial fermentation method is greatly affected by a reaction environment and is complicated in subsequent purification. Castor oil is used as a starting material in the alkali fusion cracking method, liquid diluent and catalysts are added under the condition of a high temperature and strong alkali for cracking, and finally, a cracking product is neutralized, subjected to liquid separation, acidified, filtered and dried to obtain the sebacic acid. This method is more mature, and subsequent treatment is simpler. Uniform temperature distribution plays an important role in an alkali hydrolysis reaction and has great influence on a yield of the product.

A device for preparing sebacic acid by using conventional jacket heating and alkaline hydrolysis is disclosed in the Chinese patent with No. CN 212894515 U. The conventional jacket heating has problems such as low energy utilization efficiency, large temperature gradients, and local occurrence of high temperature areas. A method for preparing sebacic acid by means of phenol-free decomposition of castor oil is disclosed in the Chinese patent with No. CN 110963909 A, in the method, microwave heating is employed to provide uniform and efficient reaction sites. However, due to limited power amplification of magnetron, amplification of a reactor is limited. Electromagnetic induction heating provides non-contact, high-efficiency and rapid heating and has the advantage of being easy in amplification, which can provide a stable reaction site for an alkaline hydrolysis reaction. However, when the reaction kettle is directly heated by means of electromagnetic induction, magnetic field distribution is affected by factors such as coil turns, which leads to uneven temperature distribution on a reactor wall surface and a large fluctuation range of temperature during the reaction of feed liquid, thus affecting the yield of prepared sebacic acid.

SUMMARY

Aiming at the above traditional technical problems existing in the prior art, an objective of the present disclosure is to provide a device and a process for preparing sebacic acid through electromagnetic induction heating coupled with dry constant-temperature alkaline hydrolysis, which have low energy consumption, a high yield, uniform temperature distribution and a small temperature fluctuation range, thereby realizing rapid, stable and uniform heating of a reaction kettle and effectively solving the problem of uneven temperature distribution of electromagnetic induction heating. There are few studies about devices for preparing sebacic acid through electromagnetic induction heating coupled with dry constant-temperature alkaline hydrolysis at home and abroad.

The objective of the present disclosure is completed by the following technical solutions:

A device for preparing sebacic acid through electromagnetic induction heating coupled with dry constant-temperature alkaline hydrolysis includes:

an electromagnetic heating cylinder and a reaction kettle arranged in the electromagnetic heating cylinder. Heat storage pellets fill space between the reaction kettle and the electromagnetic heating cylinder, and the heat storage pellets closely adhere to an inner wall of the electromagnetic heating cylinder and an outer wall of the reaction kettle, thus realizing dry constant-temperature heating. Thermal insulation cotton is wrapped around an outer side of the electromagnetic heating cylinder, tops of the heat storage pellets and an upper end of the reaction kettle, and a high temperature mica wire connected to an electromagnetic induction heating controller is wound around an outer side of a side portion of the thermal insulation cotton. The upper end of the reaction kettle is provided with a feeding port, a gas outlet and a temperature measuring port, the reaction kettle is also provided with a stirring device, and a lower portion of the reaction kettle is provided with a discharging port. The feeding port, the gas outlet, the temperature measuring port and the discharging port all extend out of the thermal insulation cotton.

Further, the upper end of the reaction kettle is connected to a sealing head by using a flange, the feeding port, the gas outlet and the temperature measuring port are all arranged on the sealing head, and a stirring port is arranged at a top of the sealing head. The stirring device includes an electric motor and a stirring paddle, and the electric motor is arranged on the stirring port. The stirring paddle is arranged at a center of an interior of the reaction kettle, and an upper end of the stirring paddle is connected to the electric motor.

Further, a thermocouple is inserted into the temperature measuring port for measuring a temperature of feed liquid in the reaction kettle, and the gas outlet is sequentially connected to a condenser and a receiving tank through pipelines.

Further, a nozzle is further arranged inside the reaction kettle, and a liquid input pipe of the nozzle penetrates out of the reaction kettle and is connected to an infusion pump. The infusion pump is connected to a material storage tank through a pipeline, and methyl ricinoleate is contained inside the storage tank. The raw material of methyl ricinoleate is sprayed in a spray feeding manner, such that the raw material of methyl ricinoleate is sprayed to a surface of the feed liquid inside the reaction kettle more uniformly.

Further, a material of the electromagnetic heating cylinder is selected from iron, cobalt, nickel or carbon steel, and the thermal insulation cotton is made of aluminum silicate, ceramic fibers or glass fibers.

Further, the electromagnetic induction heating controller heats the electromagnetic heating cylinder by means of electromagnetic induction heating with an output voltage frequency of 11-16 kHz, and a penetration depth of electromagnetic induction heating is far smaller than a thickness of the electromagnetic heating cylinder (the thickness of the electromagnetic heating cylinder being greater than 1.5 mm). The whole of the electromagnetic heating cylinder is an unsealed cylinder made of iron, cobalt, nickel, carbon steel and other materials with good magnetic conductivity, and the outer side and the bottom of the electromagnetic heating cylinder are wrapped in aluminum silicate, ceramic fiber, glass fiber and other thermal insulation cotton with a thickness of 20-40 mm and a good thermal insulation effect, such that electromagnetic induction heating efficiency and thermal efficiency of the device are improved, and the thermal insulation effect is also achieved.

Preferably, the coil of the high temperature mica wire has 10-20 turns, and the coil of the mica wire and the electromagnetic induction heating controller are connected by using insulators welded to the upper end and the lower end of the electromagnetic heating cylinder. Moreover, a k-type thermocouple is arranged at the center of the inner wall of the electromagnetic heating cylinder and connected to the electromagnetic induction heating controller for precise temperature control. A fan is mounted inside the electromagnetic induction heating controller to dissipate heat from the controller.

Further, in the present disclosure, the heat storage pellets fills the space between the electromagnetic heating cylinder and the reaction kettle, and the heat storage pellets are made of metal materials with larger thermal conductivity and heat capacity such as copper, aluminum alloy, iron and stainless steel and/or inorganic materials such as silicon carbide and have a diameter of 0.1-1 mm. Compared with a wet constant-temperature method, the dry constant-temperature heating method has the advantages of accurate temperature control, safe operation, rapid heating and convenient maintenance. A plurality of temperature measuring points are arranged inside the reaction kettle, such that real-time monitoring of the internal temperature of the reaction kettle is achieved.

The reaction kettle is made of 316 or 310 s stainless steel corrosion-resistant material to prevent corrosion of the reaction kettle by the feed liquid.

Preferably, a screw rod may be added at a bottom of the reaction kettle of the device for preparing sebacic acid through electromagnetic induction heating coupled with dry constant-temperature alkaline hydrolysis to provide assistance in discharge.

The present disclosure further provides a process for preparing sebacic acid through electromagnetic induction heating coupled with dry constant-temperature alkaline hydrolysis includes the following steps:

1) firstly, adding sodium hydroxide, water, diluent and a catalyst into a reaction kettle, and starting stirring;
2) starting an electromagnetic induction heating controller after preparation work is finished, heating an electromagnetic heating cylinder, transferring heat to the reaction kettle through heat storage pellets, and performing heating to raise a temperature of the feed liquid in the reaction kettle to 100-200° C. first, such that moisture in the feed liquid is discharged, and a boiling phenomenon is prevented from being generated during a subsequent temperature rise;
3) then, continuously raising the temperature of the feed liquid to reach an alkali hydrolysis reaction temperature of 280-310° C., spraying methyl ricinoleate into the feed liquid in the reaction kettle for a reaction, discharging a gaseous product generated by cracking from a gas outlet, and performing condensation and collection; and
4) after the reaction is finished, discharging a product in the reaction kettle from a discharging port, dissolving the product same in hot water, then neutralizing the solution with acid to make pH=6.0±0.2, separating an aqueous phase through a liquid separation operation, in this case, the main component of the solution being sebacic acid monosodium salt, performing acidification again with acid to make the pH=2.0±0.2, and then performing filtering and drying to obtain the sebacic acid.

Further, in step 1), the diluent is liquid paraffin, the catalyst is lead oxide, and a mass ratio of the sodium hydroxide to the water to the diluent and the catalyst is 1:0.8-1.2:2.5-4:0.005-0.02, and a stirring speed is 400-500 rpm.

Further, in step 2), the alkali hydrolysis reaction temperature is 290±5° C., reaction time is 4-6 h, and a mass ratio of the methyl ricinoleate to the sodium hydroxide in step 1) is 0.8-1.2:1.

The above technology is employed, and compared with the prior art, the present disclosure has the beneficial effects as follows: 1. According to the reaction device of the present disclosure, the manner of electromagnetic induction heating coupled with the dry constant temperature is employed to heat the reaction kettle, and the heat storage pellets fill the space between the electromagnetic heating cylinder and the reaction kettle to provide a uniform and stable heating place for the reaction, which not only realizes rapid, stable and uniform heating of the reaction kettle, but also effectively solves the problem of uneven temperature distribution of electromagnetic induction heating. Moreover, the dry constant-temperature heating method has the advantages of accurate temperature control, safe operation, rapid heating and convenient maintenance, and can reduce temperature fluctuation of the reaction kettle and the feed liquid in the reaction kettle.

2. Compared with alkali hydrolysis reactors commonly used at home and abroad, the device provided by the present disclosure takes shorter time to reach a stable temperature, and has the advantages of low energy consumption, high efficiency, stable operation, etc.

BRIEF DESCRIPTION OF THE DRAWINGS

In FIG. 1: 1—electromagnetic induction heating controller, 2—high temperature mica wire, 3—aluminum silicate insulation cotton, 4—electromagnetic heating cylinder, 5—heat storage pellet, 6—reaction kettle, 7—storage tank, 8—pump, 9—nozzle, 10—condenser, 11—receiving tank, 12—electric motor, 13—stirring paddle, and 14—thermocouple.

DETAILED DESCRIPTIONS OF THE EMBODIMENTS

The present disclosure is further described below in conjunction with particular examples, but the protection scope of the present disclosure is not limited herein.

Figure 1:
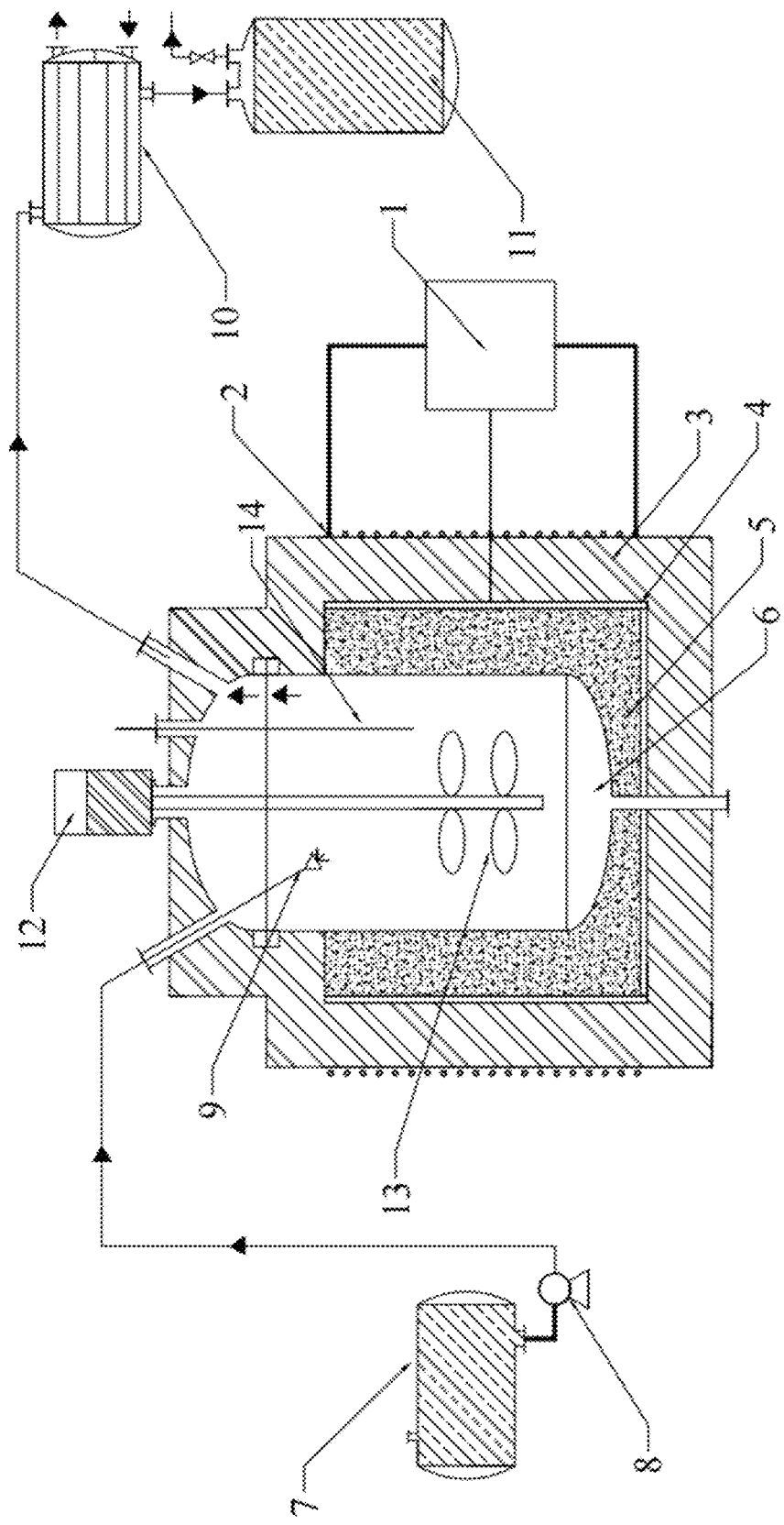
FIG. 1 is a schematic structural diagram of a device provided by the present disclosure.

Examples: referring to FIG. 1, a device for preparing sebacic acid through electromagnetic induction heating coupled with dry constant-temperature alkaline hydrolysis includes an electromagnetic induction heating controller 1, an electromagnetic heating cylinder 4, a heat storage pellet 5, thermal insulation cotton 3, a high temperature mica wire 2, a reaction kettle 6, an electric motor 12, a stirring paddle 13, a thermocouple 14, a storage tank 7, an infusion pump 8, a nozzle 9, a condenser 10 and a receiving tank 11.

An outer side of the electromagnetic heating cylinder 4 is wrapped in the thermal insulation cotton 3, and an outer side of the thermal insulation cotton 3 is provided with the high temperature mica wire 2 connected to the electromagnetic induction heating controller 1. Referring to FIG. 1, tops of the heat storage pellets 5 and an upper end of the reaction kettle 6 are also wrapped in the thermal insulation cotton 3.

The reaction kettle 6 is arranged in the electromagnetic heating cylinder 4, and the heat storage pellets 5 fill space between the reaction kettle 6 and the electromagnetic heating cylinder 4. A stirring port connected to the electric motor 12 and the stirring paddle 13 is provided at an upper portion of the reaction kettle 6, and the electric motor 12 is arranged on the stirring port. The stirring paddle 13 is arranged at a center of an interior of the reaction kettle 6, and an upper end of the stirring paddle is connected to the electric motor 12. A feeding port, a gas outlet and a temperature measuring port are provided at the upper portion of the reaction kettle 6, and a discharging port is provided at a lower portion of the reaction kettle. A thermocouple 14 enters the interior of the reaction kettle 6 through the temperature measuring port to monitor the temperature of the feed liquid during the reaction in real time. The raw material is conveyed to the nozzle 9 for feeding by means of the infusion pump 8 from the storage tank 7. Gas generated by the reaction is introduced into the condenser 10 through the gas outlet and then enters the receiving tank 11. The feed liquid in the reaction kettle is taken out through the discharging port and then is dissolved. After acidification and liquid separation, acidification, filtering and drying are performed to obtain the sebacic acid.

The upper end of the reaction kettle 6 is connected to a sealing head by using a flange, the feeding port, the gas outlet and the temperature measuring port are all arranged on the sealing head, and a stirring port is arranged at a top of the sealing head.

According to the present disclosure, methyl ricinoleate serves as the raw material, and a process for preparing sebacic acid through electromagnetic induction heating coupled with dry constant-temperature alkaline hydrolysis includes the following specific steps: 1. Firstly, add sodium hydroxide, water, diluent and a catalyst into the reaction kettle, and start stirring, where a stirring speed is 500 rpm.

2. Set a temperature of the electromagnetic induction heating controller to 190° C., stabilize the temperature for about 8 min when the temperature rises to 190° C. by means of heating, and discharge water in feed liquid to prevent boiling. Then, adjust the temperature of the controller to 300° C., and start raising the temperature. Moreover, measure the temperature of the feed liquid by the thermocouple, when the temperature of the feed liquid is stabilized at about 290° C., pump the raw material to a nozzle 9 for feeding, spray the methyl ricinoleate into the reaction kettle to start alkaline hydrolysis. Monitor temperature fluctuation of the feed liquid in the reaction kettle in real time, and control the temperature fluctuation within the range of 3° C.

3. Spray the methyl ricinoleate at this temperature for 1 h and then stop spraying. Perform a reaction for 4 h, discharge a gas product generated in the reaction process, namely secondary octanol from the gas outlet to the condenser 10, after the product taken out from the bottom of the reaction kettle is dissolved, add a sulfuric acid aqueous solution with the mass percentage of 50% for neutralization, then perform liquid separation to obtain sebacic acid monosodium salt, perform acidification again, and perform filtration and drying to obtain white solid sebacic acid.

Example 1: experiment for electromagnetic induction heating coupled with dry constant temperature In a device for preparing sebacic acid through electromagnetic induction heating coupled with dry constant-temperature alkaline hydrolysis, an electromagnetic heating cylinder 4 was made of a 2Cr13 stainless steel material with a thickness of 2 mm, a reaction kettle 6 was made of 316 stainless steel, and stainless steel heat storage pellets 5 with a diameter of 0.1 mm filled the space between the reaction kettle 6 and the electromagnetic heating cylinder 4.

Solid sodium hydroxide, water, liquid paraffin and lead oxide catalyst at a mass ratio of 1:1:3:0.01 were added to the reaction kettle by ⅓, an electric motor was started to stir a stirring paddle at 500 rpm, and then a temperature of a condenser was set to 20° C.

Figure 2:
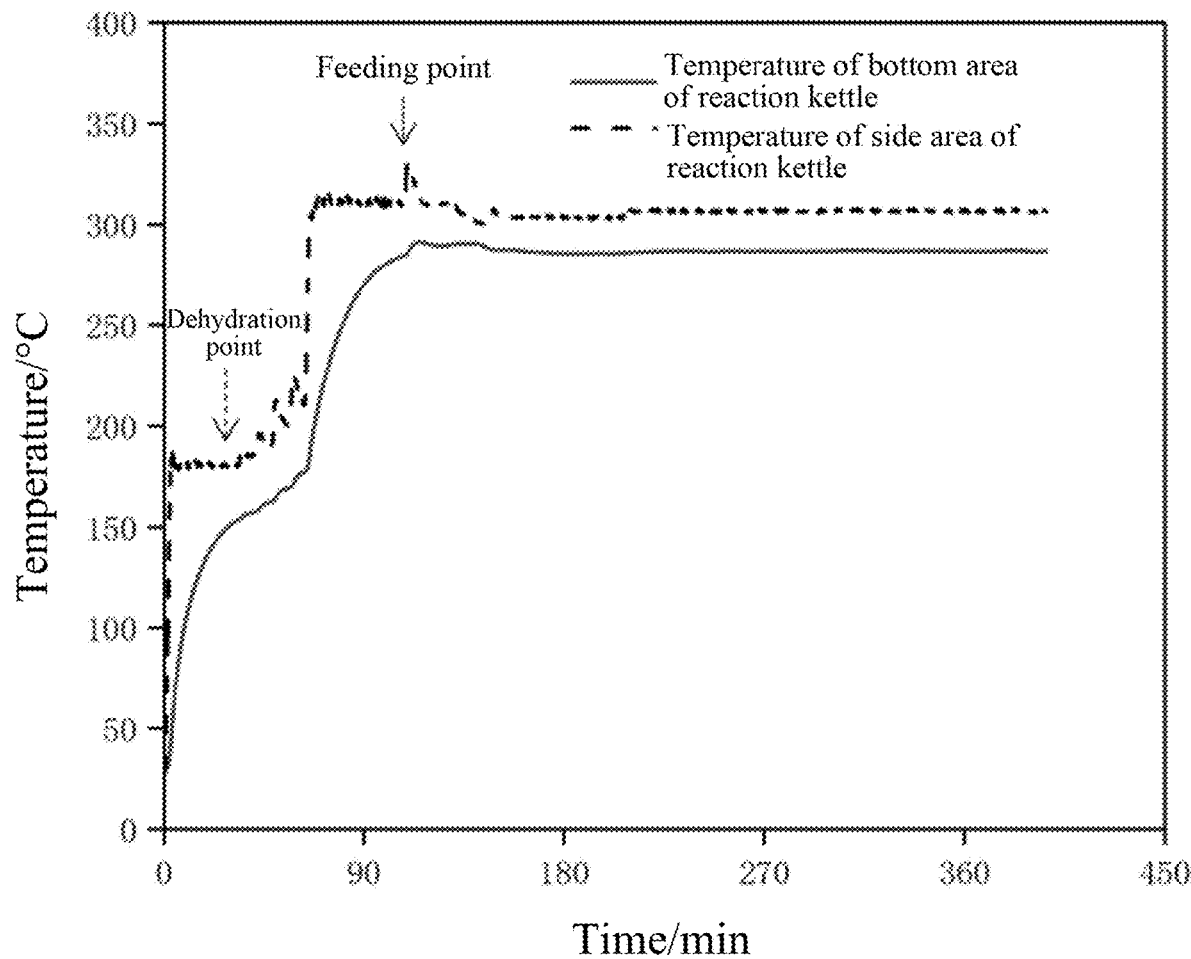
FIG. 2 is a schematic diagram for temperatures at areas of an inner wall of an electromagnetic heating cylinder, feed liquid inside a reaction kettle, and a bottom and a side portion of the reaction kettle of a device provided by the present disclosure.
Figure 3:
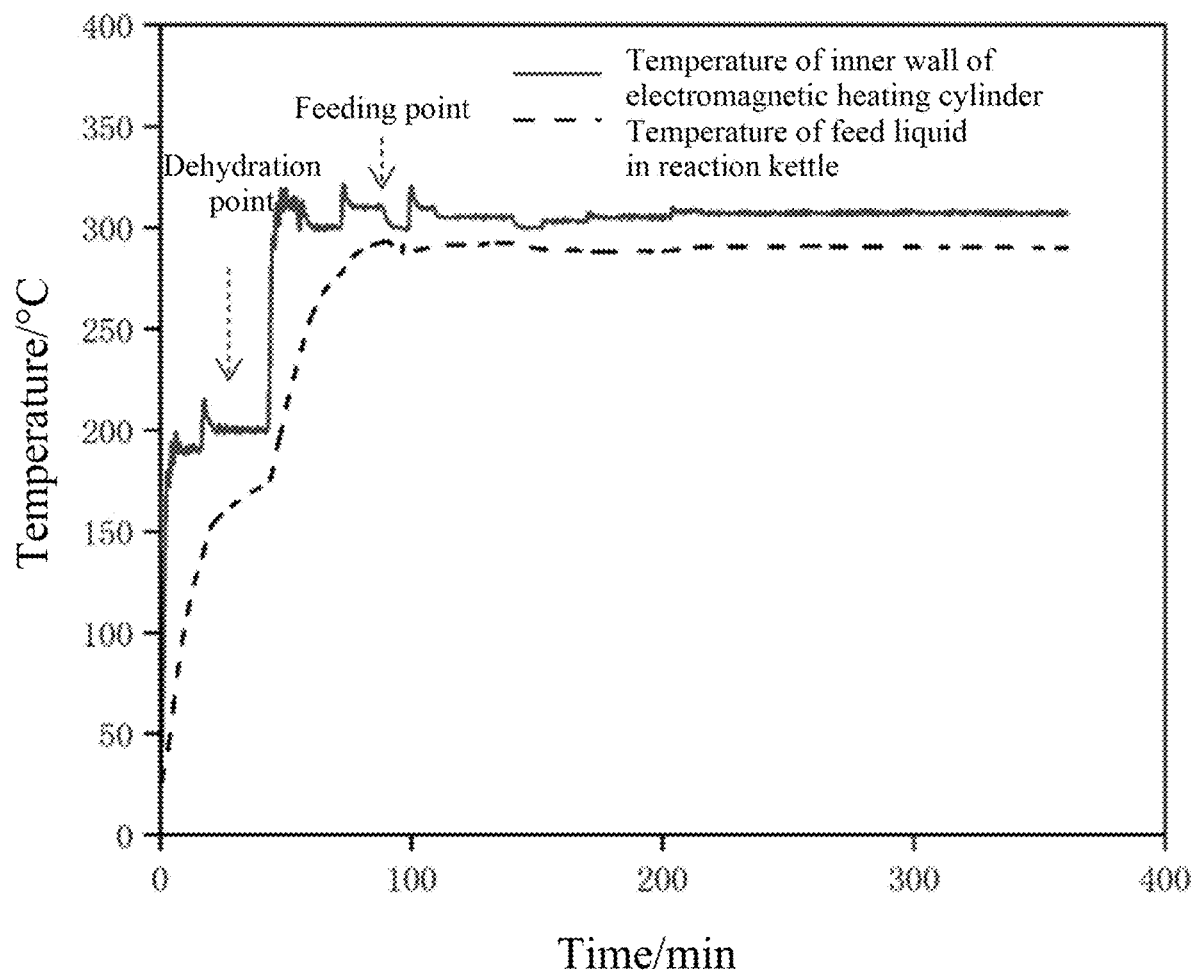
FIG. 3 is a schematic diagram for temperatures of an inner wall of an electromagnetic heating cylinder and feed liquid inside a reaction kettle of a device provided by the present disclosure.

After preparation work was completed, the electromagnetic induction heating controller is started, the temperature is set to 190° C., the temperature rise is stopped when the wall surface temperature of the electromagnetic heating cylinder is 190° C., and the temperature was stabilized for a period of time, during which water in feed liquid is discharged, so as to prevent occurrence of a boiling phenomenon during a subsequent temperature rise. Then, the temperature was set to 300° C. by the controller, when the temperature of the inner wall surface of the electromagnetic heating cylinder was stabilized at 300° C., the temperature of the feed liquid was stabilized at 290° C., then methyl ricinoleate with a mass ratio of 1:1 to solid sodium hydroxide was pumped into the nozzle in the reaction kettle from the storage tank within 1 h, and then feeding was performed in a spraying manner. In this case, the temperature of the feed liquid is monitored by a thermocouple in the reaction kettle, and the reaction was continued for 4 h, that was, the total reaction period was 5 h. A gas product generated during the reaction, namely secondary octanol, was discharged to a condenser from a gas outlet and then discharged to a receiving tank. After the reaction was finished, the product in the kettle was discharged from the discharging port and dissolved in hot water, and then the solution was neutralized with a sulfuric acid aqueous solution with the mass percentage of 50% to make the pH-6.0. In this case, a top layer of the solution was liquid paraffin, a middle layer was a by-product layer, and the lowest layer was an aqueous phase. The aqueous phase was separated by a liquid separation operation, and the main component in the aqueous phase was sebacic acid monosodium salt. Acidification was performed again with the sulfuric acid aqueous solution with the mass percentage of 50%, and the solution was adjusted to make pH=2.0. A large number of white particles were observed to precipitate, and then filtering and drying were performed to obtain white solid, namely the sebacic acid. Results are as follows: temperature rise curves of area of the bottom and the side portion of the reaction kettle of the device provided by the present disclosure are shown in FIG. 2, and temperature rise curves of the inner wall of the electromagnetic heating cylinder and the feed liquid inside the reaction kettle are shown in FIG. 3. It takes 95 min to heat the electromagnetic induction heating cylinder to reach the set reaction temperature and complete dehydration. In this case, the internal temperature of the device is stable, the temperature of the feed liquid t is 290° C., and the maximum temperature deviation of the reaction kettle is 8° C. (that is, the maximum temperature deviation between the outer wall of the side portion and the outer wall of the bottom of the reaction kettle is 8° C.). The minimum temperature of the outer wall of the bottom of the reaction kettle is 292° C., the maximum fluctuation of the internal temperature of the feed liquid is ±1° C. during the reaction (i.e., from the beginning of feeding of the methyl ricinoleate feeding to the end of reaction), and a yield of the target product of sebacic acid is 74.47%.

Example 2: experiment of electric heating dry constant temperature. The reaction operation of Example 2 is the same as that of Example 1, except that electromagnetic induction heating is replaced by resistance wire heating, that is, "electromagnetic induction heating controller 1 and high temperature mica wire 2" is replaced by "resistance wire heating controller and resistance wire".

Results of Example 2 are as follows: it takes 120 min to reach the set reaction temperature and complete dehydration by heating the electromagnetic heating cylinder with the resistance wire. In this case, the internal temperature of the device is stable, the temperature of the feed liquid is 290° C., and the maximum temperature deviation of the reaction kettle is 15° C. The maximum temperature fluctuation in the feed liquid during the reaction is ±2° C., and a yield of the target product of sebacic acid after the alkaline hydrolysis experiment is 69.9%.

Compared with the experiment of electric heating dry constant temperature in Example 2, the experiment of electromagnetic induction heating coupled with dry constant temperature in Example 1 of the present disclosure has the advantages that the product yield is increased by 4.49%, the maximum temperature deviation of the reaction kettle is reduced by 7° C., heating time is shortened by 20.83%, and energy is saved by 30%.

Example 3: The reaction operation of Example 3 is the same as that of Example 1, and the only difference lies in that "the outer side of the reaction kettle is directly wrapped around the thermal insulation cotton, and the high temperature mica wire connected to the electromagnetic induction heating controller is wound around an outer side of a side portion of the thermal insulation cotton", that is, the reaction kettle is directly heated by using electromagnetic induction in Example 3, and dry constant temperature is not employed.

Results of Example 3 are as follows: after the reaction kettle is heated to reach the set reaction temperature and dehydration is completed, the average temperature of the feed liquid is controlled at 290° C., and the maximum temperature deviation of the reaction kettle is 36° C. The temperature fluctuation in the feed liquid during the reaction is ±5° C., and a yield of the target product of sebacic acid after the alkaline hydrolysis experiment is 52.5%.

Compared with Example 3 in which the reaction kettle is directly heated by using electromagnetic induction, the experiment of electromagnetic induction heating coupled with dry constant temperature in Example 1 of the present disclosure has the advantage that the maximum deviation of the temperature of the reaction kettle is reduced by 28° C.

Example 4: The reaction operation of Example 4 is the same as that of Example 3, except that electromagnetic induction heating is replaced by resistance wire heating, that is, "electromagnetic induction heating controller 1 and high temperature mica wire 2" is replaced by "resistance wire heating controller and resistance wire", that is, the reaction kettle is directly heated by using the resistance wire in Example 4, and dry constant temperature is not employed. Results of Example 4 are as follows: after the reaction kettle is heated by using the resistance wire to reach the set reaction temperature and dehydration is completed, the average temperature of the feed liquid is controlled at 290° C., and the maximum temperature deviation of the reaction kettle is 40° C. The temperature fluctuation in the feed liquid during the reaction is ±6° C., and a yield of the target product of sebacic acid after the alkaline hydrolysis experiment is 49.5%.

It can be understood that equivalent substitutions or changes that are made by those skilled in the art on the basis of the technical solutions and invention concepts of the present disclosure should be covered within the protection scope of the present disclosure.

What is claimed is:

1. A device for preparing sebacic acid through electromagnetic induction heating coupled with dry constant-temperature alkaline hydrolysis, comprising:
   an electromagnetic heating cylinder and a reaction kettle arranged in the electromagnetic heating cylinder, wherein heat storage pellets fill space between the reaction kettle and the electromagnetic heating cylinder, the heat storage pellets adhere to an inner wall of the electromagnetic heating cylinder and an outer wall of the reaction kettle, thermal insulation cotton is wrapped around an outer side of the electromagnetic heat cylinder, tops of the heat storage pellets and an upper end of the reaction kettle, and a high temperature mica wire connected to an electromagnetic induction heating controller is wound around an outer side of a side portion of the thermal insulation cotton; and the upper end of the reaction kettle is provided with a feeding port, a gas outlet and a temperature measuring port, the reaction kettle is also provided with a stirring device, a lower portion of the reaction kettle is provided with a discharging port, and the feeding port, the gas outlet, the temperature measuring port and the discharging port all extend out of the thermal insulation cotton;
   a nozzle is further arranged inside the reaction kettle, a liquid input pipe of the nozzle penetrates out of the reaction kettle through the feeding port and is connected to an infusion pump, the infusion pump is connected to a storage tank through a pipeline, methyl ricinoleate is contained inside the storage tank, and the raw material of methyl ricinoleate is sprayed in a spray feeding manner:
   the electromagnetic induction heating controller heats the electromagnetic heating cylinder by means of electromagnetic induction heating with an output voltage frequency of 11-16 kHz, and a penetration depth of electromagnetic induction heating is smaller than a thickness of the electromagnetic heating cylinder;
   a particle size of the heat storage pellet is 0.1-1 mm, a material of the heat storage pellet is selected from copper, aluminum alloy, iron, stainless steel or silicon carbide.

2. The device for preparing sebacic acid through electromagnetic induction heating coupled with dry constant-temperature alkaline hydrolysis according to claim 1, wherein the upper end of the reaction kettle is connected to a sealing head by using a flange, the feeding port, the gas outlet and the temperature measuring port are all arranged on the sealing head, a stirring port is arranged at a top of the sealing head, the stirring device comprises an electric motor and a stirring paddle, the electric motor is arranged on the stirring port, the stirring paddle is arranged at a center of an interior of the reaction kettle, and an upper end of the stirring paddle is connected to the electric motor.

3. The device for preparing sebacic acid through electromagnetic induction heating coupled with dry constant-temperature alkaline hydrolysis according to claim 1, wherein a thermocouple is inserted into the temperature measuring port for measuring a temperature of feed liquid in the reaction kettle, and the gas outlet is sequentially connected to a condenser and a receiving tank through pipelines.

4. The device for preparing sebacic acid through electromagnetic induction heating coupled with dry constant-temperature alkaline hydrolysis according to claim 1, wherein the reaction kettle is made of 316 or 310S stainless steel.

5. A process for preparing sebacic acid through electromagnetic induction heating coupled with dry constant-temperature alkaline hydrolysis, employing the device according to claim 1 for a reaction, and comprising the following steps:
- step 1: firstly, adding sodium hydroxide, water, diluent and a catalyst into the reaction kettle, and starting stirring;
- step 2: starting the electromagnetic induction heating controller after preparation work is finished, heating the electromagnetic heating cylinder, transferring heat to the reaction kettle through the heat storage pellets, and performing heating to raise a temperature of the feed liquid in the reaction kettle to 100-200° C. first, such that moisture in the feed liquid is discharged, and a boiling phenomenon is prevented from being generated during a subsequent temperature rise;
- step 3: then, continuously raising the temperature of the feed liquid to reach an alkali hydrolysis reaction temperature of 280-310° C., spraying methyl ricinoleate into the feed liquid in the reaction kettle for a reaction, discharging a gaseous product generated by cracking from the gas outlet, and performing condensation and collection; and
- step 4: after the reaction is finished, discharging a product in the reaction kettle from the discharging port, dissolving the product in hot water, then neutralizing the solution with acid to make pH=6.0±0.2, separating an aqueous phase through a liquid separation operation, performing acidification again with acid to make the pH=2.0±0.2, and then performing filtering and drying to obtain the sebacic acid.

6. The process according to claim 5, wherein in step 1, the diluent is liquid paraffin, the catalyst is lead oxide, and a mass ratio of the sodium hydroxide to the water is 1:0.8-1.2;
a mass ratio of the sodium hydroxide to the diluent is 1:2.5-4; and
a mass ratio of the sodium hydroxide to the catalyst is 1:0.005-0.02, and a stirring speed is 400-500 rpm.

7. The process according to claim 5, wherein in step 3, the alkali hydrolysis reaction temperature is 290±5° C., reaction time is 4-6 h, and a mass ratio of the methyl ricinoleate to the sodium hydroxide is 0.8-1.2:1.

* * * * *